US007897727B2

(12) United States Patent
Farach-Carson et al.

(10) Patent No.: US 7,897,727 B2
(45) Date of Patent: Mar. 1, 2011

(54) BIOACTIVE PEPTIDE FOR CELL ADHESION

(75) Inventors: Mary C. Farach-Carson, Hockessin, DE (US); Daniel D. Carson, Hockessin, DE (US); Jeffrey B. Safran, Bear, DE (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 12/398,534

(22) Filed: Mar. 5, 2009

(65) Prior Publication Data

US 2009/0239304 A1 Sep. 24, 2009

Related U.S. Application Data

(62) Division of application No. 10/363,376, filed as application No. PCT/US01/26640 on Aug. 27, 2001.

(60) Provisional application No. 60/229,222, filed on Aug. 31, 2000, provisional application No. 60/309,209, filed on Aug. 1, 2001.

(51) Int. Cl.
*C07K 14/00* (2006.01)
(52) U.S. Cl. .................... 530/350; 530/300; 435/7.1
(58) Field of Classification Search ........................ None
See application file for complete search history.

(56) References Cited

U.S. PATENT DOCUMENTS

| 6,262,017 | B1 | 7/2001 | Dee et al. | |
|---|---|---|---|---|
| 7,081,345 | B1 * | 7/2006 | Roecklin et al. | 435/7.1 |
| 7,510,843 | B2 * | 3/2009 | Roecklin et al. | 435/7.1 |
| 2004/0009474 | A1 | 1/2004 | Leach et al. | |

FOREIGN PATENT DOCUMENTS

WO WO 01/90366 5/2000

OTHER PUBLICATIONS

Chakravarti, et al., "Recombinant Domain III of Perlecan Promotes Cell Attachment Through Its RGDS Secquence," *The Journal of Biological Chemistry*, Jan. 1995, 270(1), pp. 404-409.
Cohen, et al., "Structural Characterization of the Complete Human Perlecan Gene and Its Promoter," *Proc. Natl. Acad. Sci. USA*, Nov. 1993, vol. 90, pp. 10404-10408.
Hopf, et al., "Recombinant Domain IV of Perlecan Binds to Nidogens, Laminin-Nidogen Complex, Fibronectin, Fibulin-2 and Heparin," *Eur. J. Biochem*, 1999, vol. 259, pp. 917-925.
Hopf, et al., "Mapping of Binding Sites for Nidogens, Fibulin-2, Fibronectin and Heparin to Different IG Modules of Perlecan," *J. Mol. Biol.*, 2001, vol. 311, pp. 529-541.
Iozzo, Renato V.; "Matrix Proteoglycans: From Molecular Design to Cellular Function," *Annu. Rev. Biochem.*, 1998, vol. 67, pp. 609-652.
Hayashi, et al., "Endothelial Cells Interact with the Core Protein of Basement Membrane Perlecan through β1 and β2 Integrins: An Adhesion Modulated by Glycosaminoglycan," *The Journal of Cell Biology*, Nov. 1992, 119(4), pp. 945-959.
Lebaron, Richard G. and Athanasiou, Kyriacos A., "Extracellular Matrix Cell Adhesion Peptides: Functional Applications in Orthodpedic Materials," *Tissue Engineering*, 2000, vol. 6(2) pp. 85-103.
Massia, S.P., Hubbell, J.A.; "Human endothelial cell interactions with surface-coupled adhesion peptides on a nonadhesive glass substrate and two polymeric biomaterials," Journal of Biomedical Materials Research, 1991, vol. 25, No. 2, pp. 223-242.
Murdoch, et al., Primary Structure of the Human Heparan Sulfate Proteoglycan from Basement Membrane (HSPG2/Perlecan), *The Journal of Biological Chemistry*, Apr. 25, 1992, vol. 267, No. 12, pp. 8544-8577.
Newton, et al., "Residues on Both Faces of the First Immunoglobulin Fold Contribute to Homophilic Binding Sites of PECAM-1/CD31," *The Journal of Biological Chemistry*, 272(33), Aug. 15, 1997, pp. 20555-20563.
Noonan, et al., "The Complete Sequence of Perlecan, a Basement Membrane Heparan Sulfate Proteoglycan, Reveals Extensive Similarity with Laminin A Chain, Low Density Lipoprotein-Receptor, and the Neural Cell Adhesion Molecule." *The Journal of Biological Chemistry*, 266(34), Dec. 5, 1991, pp. 22939-22947.
Puleo, D.A., "Immobilization of Protein on Silanized Orthopedic Biomaterials," *Materials Research Society Symposium*, 1994, vol. 331, pp. 269-275.
Seffernick, et al., "Melamine Deaminase and Atrazine Chlorohydrolase: 98 Percent Identical but Functionally Different," *Journal of Bacteriology*, Apr. 2001, vol. 183, pp. 2405-2410.
Sharma, et al., "Antisense Targeting of Perlecan Blocks Tumor Growth and Angiogenesis in Vivo," *J. Clin. Invest.*, Oct. 1998, vol. 102, No. 8, pp. 1599-1608.
Sundarraj, et al., "Perlecan is a Component of Cartligae Matrix and Promotes Chondrocyte Attachment," *Journal of Cell Science*, 1995, vol. 108, pp. 2663-2672.
Sweigert, et al., "Review: Toward Tissue Engineering of the Knee Meniscus," *Tissue engineering*, 7(2), 2001, pp. 111-129.
Weismann, et al., "Ligand-binding sites in Ig-like domains of receptor tyrosine kinases," *J. Mol. Med.* 78:247-260 (2000).
Wells, James A., "Additivity of Mutational Effects in Proteins," *Biochemistry*, Sep. 18, 1990, vol. 29, No. 37, pp. 8509-8517. Mikos, Antonios G. et al., "Biomaterials for Drug and Cell Delivery," Materials Research Society Symposium Proceedings; Materials Research Society 1994; materials Research Society, Pittsburg, Pennsylvania; vol. 331; pp. 269-275.
NIH-MGC, National Institutes of Health, Mammalian Gene Collection (MGC), Sep. 2000, Acc. No. BE747501.
NIH-MGC, National Institutes of Health, Mammalian Gene Collection (MGC), Jul. 2000, Acc. No. BE291062.

* cited by examiner

*Primary Examiner* — Hope A. Robinson
(74) *Attorney, Agent, or Firm* — RatnerPrestia

(57) ABSTRACT

Implantable devices for adhering eukaryotic cells and devices providing a substrate for eukaryotic cell growth and/or differentiation in vitro are described. Each device comprises a scaffold that is coated with a protein comprising an adhesive polypeptide that has at least 90% sequence identity to a specific peptide sequence within domain IV of perlecan. The devices adhere epithelial cells, epithelial stem cells, mesenchymal stem cells, and osteoblasts.

15 Claims, 13 Drawing Sheets
(9 of 13 Drawing Sheet(s) Filed in Color)

SEQUENCE LISTING

```
<160> NUMBER OF SEQ ID NOS: 4

<210> SEQ ID NO 1
<211> LENGTH: 17
<212> TYPE: PRT
<213> ORGANISM: Homo sapiens

<400> SEQUENCE: 1

Thr Trp Ser Lys Val Gly Gly His Leu Arg Pro Gly Ile Val Gln Ser
1               5                   10                  15

Gly

<210> SEQ ID NO 2
<211> LENGTH: 51
<212> TYPE: DNA
<213> ORGANISM: Homo sapiens

<400> SEQUENCE: 2
acatggagca aagttggagg gcacctgcgg ccaggcattg tgcagagcgg a              51

<210> SEQ ID NO 3
<211> LENGTH: 51
<212> TYPE: DNA
<213> ORGANISM: Mus musculus

<400> SEQUENCE: 3
acatggagca aagtcggggg acacctacgg cctggcatcg tgcaaagcgg a              51

<210> SEQ ID NO 4
<211> LENGTH: 17
<212> TYPE: PRT
<213> ORGANISM: Artificial
<220> FEATURE:
<223> OTHER INFORMATION: completely synthesized

<400> SEQUENCE: 4

Thr Gly Lys Ser Val Gly Gly Ser Leu Ile Trp Pro Val Arg Gly Gln
1               5                   10                  15

His
```

BIOACTIVE PEPTIDE FOR CELL ADHESION

CROSS REFERENCE TO RELATED APPLICATIONS

This is a divisional application of U.S. application Ser. No. 10/363,376 (status: allowed), filed Jul. 7, 2003, which is a National Phase Application of PCT Application Ser. No. US01/026640, filed Aug. 27, 2001, which claims the benefit of U.S. Provisional Application Ser. No. 60/229,222, filed Aug. 31, 2000, and U.S. Provisional Application Ser. No. 60/309,209, filed Aug. 1, 2001, all of which are incorporated herein, in entirety, by reference.

GOVERNMENT INTERESTS

This invention was made with government support under Grant Nos. HD25235 ; DE13542, RR16458, and CA098912, Project 2, awarded by the National Institutes of Health. The government has certain rights in this invention.

BACKGROUND OF THE INVENTION

Perlecan is a heparan sulfate proteoglycan (Noonan, D. M. (1991) *J. Biol. Chem.* (266) 34: 22939-22947). The proteoglycan family contains more than 30 members that perform an assortment of biological functions and are widely distributed in basement membranes. Proteoglycans act as tissue organizers and as biological filters, affect cell growth, and have growth factor activities (Iozzo, R. V. (1998) *Annu. Rev. Biochem.* 67: 609-652). Perlecan, also known as HSPG2, is a constituent of all basement membranes and plays a role in cell adhesion, angiogenesis, cell proliferation, and tumor development (Sharma, B. (1998) *J. Clin. Invest.* (102) 8: 1599-1608). Perlecan consists of three heparan sulfate side chains attached to a large core protein consisting of five modular domains.

Perlecan Domains

Domain I contains a signal peptide and a unique 172 amino acid sequence that contains the heparan sulfate binding sites. Domain I has no internal repeats and is devoid of cysteine residues. This domain is enriched with acidic amino acid residues that facilitate the heparan sulfate attachment (Iozzo, R., supra). Domain II contains four cysteines and acidic amino acid rich repeats similar to those found in the low-density lipoprotein receptor (LDLr). Domain III contains cysteine-rich globular regions similar to the short arm of the laminin A chain. Domain IV is the largest and most repetitive domain because it contains 14 and 21 immunoglobulin repeats in the murine and human species, respectively (Iozzo, R., supra). Domain V contains three laminin type repeats and four repeats similar to epidermal growth factor. This domain is homologous to the globular terminus of the laminin A chain.

Rotary shadowing revealed perlecan to be a series of globules separated by rods creating the appearance of beads on a string, hence the name perlecan. Perlecan is derived from the Middle English "perle" meaning pearl and "can" signifying the posttranslational glycosaminoglycan modification (Noonan, D. M., supra).

Work by Cohen et al. showed that perlecan has multiple sites of transcription initiation, which suggests that the various transcripts observed with perlecan are more likely due to alternative splicing of internal exons than due to differential usage of polyadenylation sites (Cohen, I. (1993) *Proc. Nat. Acad. Sci.* 90: 10404-10408).

Cell Adhesion

Work by SundarRaj et al/ showed that purified perlecan promoted the attachment of immortalized rat chondrocytes in vitro (SundarRaj, N. (1995) *J. Cell Sci.* 108 (Pt 7): 2663-2672). Chakravarti et al. studied an Arginine-Glycine-Aspartic Acid-Serine ("RGDS") amino acid sequence located in domain III that was associated with cell adhesion (Chakravarti, S. (1995) *J. Biol. Chem.* (270) 1: 404-409). Chakravarti et al. produced domain III as a recombinant protein and evaluated its cell adhesion activity. Recombinant domain III coated on tissue culture dishes supported adhesion of a mouse mammary tumor cell line in a dose dependent manner, Forty percent of the cells attached at the maximum dose. Furthermore, all of the attachment could be abolished with synthetic RGDS peptide. Chakravarti et al. concluded that the RGDS sequence is the only binding site in their recombinant domain III protein.

Hayashi et al. studied full-length perlecan and reported a higher percentage attachment of cells than Chakravarti et al. reported with just domain III (Hayashi, K. (1992) *J. Cell Biol.* 119 (4): 945-959).

Hopf et al. assessed the protein-protein interaction between domain IV of mouse perlecan and fibronectin, nidogen-1, nidogen-2, laminin-1-nidogen-1 complex, fibulin-2, and collagen IV (Hopf, M (1999) Eur. J. Biochem. 259 (3): 917-925). Hopf et al. created two separate recombinant molecules from domain IV. One consisted of the IG 2-9 modules of domain IV and had a molecular weight of 100 kD (IV-1). The second consisted of the IG modules 10-15 and had a molecular weight of 66 kDa (IV-2). Hopf et al. found that there was strong protein-protein interaction between IV-1 and fibronectin, nidogen-1, nidogen-2 and the laminin-1-nidogen-1 complex, while the IV-2 fragment had a much more restricted protein-protein interaction with weaker binding to fibronectin and fibulin-2.

Scaffolding for Tissue Repair

Numerous skeletal and connective-tissue related disorders have been treated with engineered implants. For example, implants made of substrates such as ceramics, metals, polymers, and biological composites have been used to repair bone and tissue. Improved understanding of cellular and molecular events that occur at the interface between tissues and implants is beginning to allow new approaches to implant design. Preferably, implants are designed to elicit specific, clinically-desirable responses from living cells and tissues in a patient's body. For example, it is desirable for osteoblasts to rapidly deposit mineralized matrix on the surface of (or in close apposition to) newly implanted prostheses. The swift deposition of bone stabilizes the prosthesis and minimizes motion-induced damage to surgically traumatized tissue at the implantation site.

Anchorage-dependent cells (such as osteoblasts) must first adhere to a surface in order to perform subsequent cellular functions (e.g., proliferation, deposition of bone tissue, etc.). Because cell adhesion is needed for subsequent events, methods for promoting cell adhesion are of considerable interest. The effects on cell adhesion of peptides immobilized on the surfaces of substrates have been reported. Substrates have included polymers (Massia et al. (1991) *J. Biomed. Natl.* 25: 223-242) and dental/orthopedic implant materials such as Cobalt-Chromium-Molybdenum alloy (Mikos et al. (1994) *Biomatis. Cell and Drug Delivery* 331: 269-274). Adhesion-related peptides that have been attached to substrates have included integrin-binding peptides, such as those that contain the Arginine-Glycine-Aspartic Acid (RGD) sequence. U.S. Pat. No. 6,262,017 "Peptides for Altering Osteoblast Adhesion," issued Jul. 17, 2001, discloses polypeptide coatings for controlling osteoblast adhesion to implants.

Although it is known that perlecan is involved in cell adhesion, the intact molecule is too large to exploit commercially as a cellular adhesive. Its size does not allow for efficient and cost effective commercial production. Embodiments of the present invention avoid this problem and meet the needs of the art by providing a small molecule with strong and selective cell adhesion properties.

BRIEF SUMMARY OF THE INVENTION

An implantable device for adhering eukaryotic cells is described. The device comprises a scaffold coated with an isolated protein comprising a polypeptide, the polypeptide having at least 90% sequence identity to SEQ ID NO: 1, wherein the eukaryotic cells adhere to the polypeptide. The device may be implanted or used in vitro. Also described is an implantable product for repair of tissue or an organ in vivo, the product made by the process of: (a) coating a scaffold with an isolated protein comprising a polypeptide, the polypeptide having at least 90% sequence identity to SEQ ID NO:1 and exhibiting adhesiveness to eukaryotic cells; (b) placing the scaffold in vitro along with a plurality of the eukaryotic cells; (c) permitting a plurality of the eukaryotic cells to adhere to the scaffold in vitro; and (d) permitting the adherent cells to replicate or replicate and differentiate on the scaffold.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
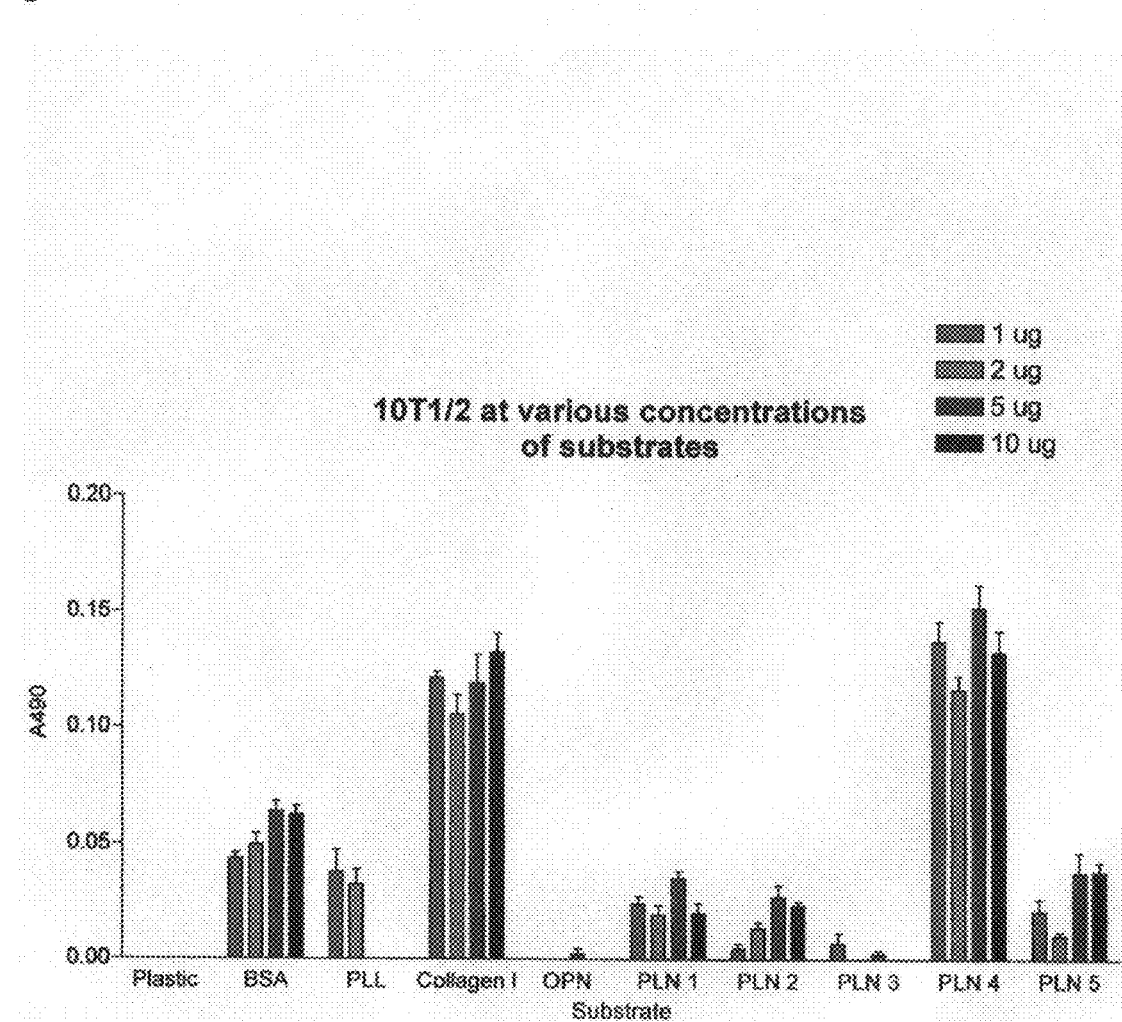
FIG. 1 depicts the 10T1/2 cell adhesion at various concentrations of substrates.

Embodiments of the invention provide polypeptides derived from the perlecan core protein as coatings for scaffolds, such as implantable tissue scaffolds. These coatings allow strong and selective cell adhesion to the scaffold. For example, such polypeptides can be coated on matrices implanted in damaged tissue such as bone or cartilage to increase the adhesion of desirable biological materials to the repair site.

Embodiments of the present invention also concern a polypeptide derived from perlecan that facilitates cell adhesion. The adhesive polypeptide has the following amino acid sequence: TWSKVGGHLRPGIVQSG (SEQ ID NO: 1). This adhesive polypeptide is derived from domain IV of the perlecan protein. The perlecan domains are disclosed in Noonan, D. M. et al., "The Complete Sequence of Perlecan . . . ", *J. Biol. Chem.* 266:34, pp. 22939-47 (Dec. 5, 1991), which is incorporated herein by reference in its entirety.

Adhesion of cells to scaffolds such as those used in tissue engineering for cartilage and bone repair, stents, or bone prosthetic devices is facilitated by coating the scaffold with the peptides described herein. The peptide coating supports rapid formation of adhesion plaques or focal adhesions of mesenchymal stem cells. The peptides also may be attached to a solid support, such as a gel column, and used to extract or purify proteins or cells that preferentially bind to the peptide. For example, such a separation may be useful for identifying cell receptors by affinity chromatography.

Preferably, the scaffold is made of a polymer, a biologically derived material, ceramic, metal, or combinations thereof, that is biologically inert and physiologically compatible with mammalian tissues. The scaffold material preferably does not induce an inflammatory response. The scaffold also preferably is capable of associating with an adhesive peptide at sufficient levels to satisfy the intended objective, e.g., increased cell adhesion at the scaffold. The scaffold preferably can bind an adhesive peptide either covalently or non-covalently, such as by electrostatic charge or hydrophobic or hydrophilic interactions.

Preferred polymers are polyamides, polypeptides, polyesters, polycarbonates, polyurethanes, polyacetals, polysaccharides, and polyolefins. Specific examples of such polymers include silicone rubber, polyurethane rubber, polyethylene, polyvinyl chloride, poly (hydroxyethyl methacrylate), poly (methyl methacrylate), poly (ethyleneterephthalate), polypropylene, polystyrene, poly (tetrafluoroethylene), polyglycolic acid, cellulose, ethylcellulose, methylcellulose, dextran, carboxymethylcellulose, hyaluronic acid, hydroxypropylmethylcellulose, nylon, collagen, and collagen-GAG. Preferred polymers include expanded polytetrafluoroethylene composed of two polymers and having nine billion pores per square inch. Additionally, the scaffold can be a copolymer, composite or blend of the above polymers.

The polymer may have other materials embedded in it, such as carbon fibers or carbon nanotubes. For example, the polymer may be comprised of carbon fibers embedded in a polyurethane-poly(L-lactide) matrix. Additional scaffold materials are disclosed in Sweigart, M. A. (2001) *Tissue Engineering* 7 (2): 111-128, which is incorporated herein by reference in its entirety. Additional scaffold materials are known to those skilled in the art.

Preferred biologically derived materials are matrices comprised of collagen sponge, cortical bone chips, cancellous-bone chips, cortico-cancellose bone chips, hydroxyapatite or like ceramics, bioactive glass, growth factors and demineralized bone, which are imbedded or suspended in a carrier material. The carrier material is preferably a fibrin-containing composition that coagulates, collagen formulations, hydroxylapatite, pleuronic polymers, synthetic or natural polymers, carboxymethylcellulose, gelatin, or combinations thereof. More preferably, the carrier is gelatin derived from human or animal tissue. Other preferred biologically derived materials are mammalian tissues, such as perichondral tissue and periosteal tissue.

Embodiments of the invention also concern isolated nucleic acid molecules comprising a nucleotide sequence of less than 11,000 nucleotides in length and preferably of less than 2,100 nucleotides in length and encoding the adhesive polypeptide described herein or biologically active portions thereof, as well as nucleic acid fragments suitable as primers or hybridization probes for the detection of nucleic acid encoding the adhesive polypeptide (e.g., mRNA). In particularly preferred embodiments, the isolated nucleic acid molecule consists of less than 11,000 nucleotides in length, and preferably less than 2,100 nucleotides and comprises the nucleotide sequence of acatggagcaaagtcggggdacac-ctacggcctggc-atcgtgcaaagcgga (SEQ ID NO:3) (mouse) or the nucleotide sequence of acatggagcaaagttggagggcacct-gcggccaggcattgtgcagagcgga (SEQ ID NO:2) (human), or a complement of either of these. In other particularly preferred embodiments, the isolated nucleic acid molecule of certain embodiments of the invention comprises a nucleotide sequence of less than 11,000 nucleotides in length, and preferably of less than 2,100 nucleotides in length, which encodes naturally occurring allelic variants, genetically altered variants and non-human homologues of the adhesive peptides described herein. Such nucleic acid molecules are identifiable as containing a nucleotide sequence of sixty or less nucleotides that is able to hybridize to or which is at least about 60-65%, preferably at least about 70-75%, more preferably at least about 80-85%, and even more preferably at least about 90-95% or more homologous to the nucleotide sequence shown in SEQ ID NO:2 or SEQ ID NO:3.

To determine the percent homology of two amino acid sequences or of two nucleic acid sequences, the sequences are aligned for optimal comparison purposes (e.g., gaps can be introduced in the sequence of one polypeptide or nucleic acid for optimal alignment with the other polypeptide or nucleic acid). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

In other embodiments, the nucleic acid is less than 11,000 nucleotides in length, and preferably less than 2,100 nucleotides in length, and encodes a polypeptide that is at least about 70-75%, still more preferably at least about 80-85%, still more preferably at least about 90-95%, and most preferably 100% homologous to the amino acid sequence of SEQ ID NO:1. In another preferred embodiment the nucleic acid molecule is less than 11,000 nucleotides in length and preferably less than 2,100 nucleotides in length and encodes a polypeptide comprising at least 15 contiguous amino acids of SEQ ID NO:1. In addition to naturally-occurring allelic variants of the adhesive polypeptide sequence that may exist in the population, the skilled artisan will further appreciate that changes can be introduced by mutation into the nucleotide sequence of SEQ ID NO:2 or SEQ. ID. NO:3, thereby leading to changes in the amino acid sequence of the encoded adhesive polypeptide, without altering the functional ability of the adhesive polypeptide. For example, nucleotide substitutions leading to amino acid substitutions at "non-essential" amino acid residues can be made in the sequence of SEQ ID NO:2 or SEQ. ID. NO:3. A "non-essential" amino acid residue is a residue that can be altered from the wild-type sequence of the adhesive polypeptide (e.g., the sequence of SEQ ID NO:1) without altering the activity, whereas an "essential" amino acid residue is required for adhesive activity.

In another embodiment, the nucleic acid molecule is less than 11,000 nucleotides in length, and preferably less than 2,100 nucleotides in length and encodes a polypeptide or portion thereof wherein the polypeptide or portion thereof includes an amino acid sequence which is sufficiently homologous to the amino acid sequence of SEQ ID NO:1, e.g., sufficiently homologous to an amino acid sequence of SEQ ID NO:1 such that the polypeptide or portion thereof maintains an adhesive activity, such as the types of adhesive activity disclosed herein.

Another aspect of certain embodiments of the invention pertain to vectors, e.g., recombinant expression vectors, containing the nucleic acid molecules described herein and host cells into which such vectors have been introduced. In one embodiment, such a host cell is used to produce an adhesive polypeptide by culturing the host cell in a suitable medium. If desired, the adhesive polypeptide can then be isolated from the medium or the host cell.

Embodiments of the invention also includes adhesive polypeptides of less than 3,700 amino acids in length and preferably of less than 700 amino acids, still more preferably of less than 100 amino acids, and comprising an amino acid sequence having at least about 70-75%, still more preferably at least about 80-85%, still more preferably at least about 90%, and most preferably 100% homology to the amino acid sequence of SEQ ID NO:1. In another preferred embodiment, the polypeptides have conservative amino acid substitutions at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in the adhesive polypeptide is preferably replaced with another amino acid residue from the same side chain family. Preferably, the polypeptide maintains the ability to adhere cells, particularly to adhere cells capable of differentiating into connective tissue cells such as bone, cartilage, tendon, ligament and so forth. Preferably, if the polypeptide is naturally occurring, it is isolated for purposes of certain embodiments of the invention.

In one embodiment, the biologically active portion of the adhesive polypeptide of SEQ ID NO:1 includes a domain or motif, preferably a domain or motif which has adhesive activity. Alternatively, the adhesive polypeptide can be of less than 3,700 amino acids in length, and preferably of less than 700 amino acids in length and comprise an amino acid sequence which is encoded by a nucleotide sequence which contains a sequence of about sixty nucleotides or less that is at least about 80-85%, and more preferably at least about 90-95%, and more preferably 100% homologous to the nucleotide sequence of SEQ ID NO:2 or SEQ ID NO:3, such as the allelic variants and non-human and non-mouse homologues of the adhesive polypeptides described herein as well as genetically altered variants generated by recombinant DNA methodologies. It is also preferred that the adhesive polypeptide have one or more of the adhesive activities described herein.

In another preferred embodiment, the polypeptide comprises the amino acid sequence of SEQ ID NO:1 and has less than 3,700 amino acids, more preferably less than 2,500 amino acids, more preferably less than 700 amino acids, even more preferably less than 500 amino acids, and still more preferably less than 100 amino acids. Polypeptide embodiments of the invention may be glycosylated or phosphorylated, such as at the serine or threonine residues. Also preferred is a polypeptide of a molecular weight of less than 100 kDa, preferably of less than 4 kDa, still more preferably of less than 2 kDa, comprised of the polypeptide of SEQ ID NO: 1.

In another preferred embodiment, the polypeptides described herein are selectively adhesive for certain cell types. For example, the polypeptides exhibit cellular specificity for undifferentiated fibroblasts (such as multipotent mouse mesenchymal stem cells, also called 10 T1/2), and epithelial-derived cell lines (such as human epithelial cells from the uterine wall ("HES") and prostate cancer cells ("PC3")).

The adhesive polypeptides described herein may be synthesized in various ways, such as by chemical synthesis or recombinant production. It is within the knowledge and skill of one in the art to prepare the polypeptides and nucleic acids described herein.

The polypeptides described herein can be operatively linked to a linker or carrier material. The linker or carrier attaches to the scaffold, allowing increased mobility for the adhesive polypeptide attached to the free end of the linker.

Preferred linkers include bovine serum albumin (BSA), fibronectin, fragments of fibronectin, collagen, fragments of collagen, and polymers, such as polyamides, polypeptides, polyesters, polycarbonates, polyurethanes, polyacetals, polysaccharides, and polyole fins. Of the polypeptide linkers, preferred are polylysine and polyalanine.

The adhesive polypeptides may be attached to the linker either covalently or non-covalently. Other linkers are readily apparent to those of skill in the art.

The adhesive polypeptides described herein, or portions or fragments thereof, can be used to prepare anti-adhesive polypeptide antibodies. Accordingly, embodiments of the invention also provide an antigenic peptide which comprises at least 8 amino acid residues of the amino acid sequence shown in SEQ ID NO:1 and encompasses an epitope of the adhesive polypeptide such that an antibody raised against the peptide forms a specific immune complex with the adhesive polypeptide. Preferably, the antigenic peptide comprises at least 10 amino acid residues, more preferably at least 15 amino acid residues, even more preferably 17 amino acid residues. Embodiments of the invention further provide an antibody that specifically binds the adhesive polypeptide. In one embodiment, the antibody is monoclonal. In another embodiment, the antibody is coupled to a detectable substance. In yet another embodiment, the antibody is incorporated into a pharmaceutical composition comprising the antibody and a pharmaceutically acceptable carrier. The antibodies described herein can be used inter alia to screen for the presence of the adhesive polypeptide in biological samples.

Another aspect of certain embodiments of the invention pertains to methods for detecting the presence of the adhesive polypeptide, or allelic variants thereof, in a biological sample. In a preferred embodiment, the methods involve contacting a biological sample (e.g., a cartilage or smooth muscle cell sample) with a compound or an agent capable of detecting the adhesive polypeptide or the mRNA encoding the adhesive polypeptide such that the presence of the adhesive polypeptide is detected in the biological sample.

The peptides described herein have a variety of uses. In one application, the peptides are attached covalently or electrostatically to scaffolds used for bone repair and reconstruction. The scaffold may be coated with a peptide described herein and the coated scaffold then contacted with bone cell precursors (mesenchymal stem cells from bone marrow, periosteum, endosteum, etc.) before implantation. Alternatively, the scaffold may be coated with the adhesive polypeptide and then implanted, such that the polypeptide adheres to naturally occurring cells in vivo. The peptide-coated scaffolds also may be used in treating tooth and jaw defects in cases of trauma, bone loss, tooth loss, and gum disease. The peptide-coated scaffolds also are useful in treating cartilage defects such as those which result from rheumatoid arthritis, osteoarthritis and trauma. Cells useful for seeding in such circumstances include chondroblasts and chondrocytes and cartilage cell precursors such as the cell precursors described above in connection with bone. The scaffolds also may be used to repair defects and damage in skin, muscle and other soft tissues such as results from trauma, burns, ulcers (diabetic ulcers, pressure sores, venus, stasis ulcers, etc.). In this case, peptide-coated scaffolds can be seeded with, for example, dermal fibroblasts, keratinocytes, and skeletal muscle cells. Likewise, damage to visceral organs including liver damage, heart attack damage, and damage resulting from intestinal cancer or intestinal ulcer may be treated with the peptide-coated scaffolds described herein. In these instances, the peptide-coated scaffolds can be seeded with cells such as hepatocytes, cardiac muscle cells, intestinal cells, etc.

Embodiments of the invention are also directed to devices for implantation in a mammal comprising a scaffold coated with one or more of the polypeptides described herein. Preferably the device comprises a scaffold attached to a linker to which one of the polypeptides described herein has been attached.

Embodiments of the invention also pertain to in vitro culture of cells with the purpose of creating tissue constructs for repairing tissues and organs in vivo. The scaffolds may be used to promote tissue culture of committed cells and/or differentiation of precursor cells. Thus, the scaffolds described herein can be used in virtually all instances when it is desirable to provide a substrate for the growth of cells onto or into a tissue replaceable matrix. Scaffolds can also be used with autografts, allografts, and xenografts associated with bone grafts, cartilage grafts, and joint resurfacing implants.

The terms "peptide", "polypeptide", and "protein" are used interchangeably herein.

As used herein, the term "nucleic acid molecule" is intended to include DNA molecules (e.g., cDNA or genomic DNA) and RNA molecules (e.g., mRNA) and analogs of the DNA or RNA generated using nucleotide analogs.

The nucleic acid molecule can be single-stranded or double-stranded, but preferably is double-stranded DNA. An "isolated" nucleic acid molecule is one that is separated from other nucleic acid molecules that are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be substantially free of other cellular material, or culture medium when produced by recombinant techniques, or chemical precursors or other chemicals when chemically synthesized.

An "isolated" peptide, polypeptide or protein is one that is separated from other polypeptides that are present in the natural source of the polypeptide.

As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6.times. sodium chloride/sodium citrate (SSC) at about 45° C., followed by washing in 0.2.times.SSC, 0.1% SDS at 50-65° C. Preferably, an isolated nucleic acid molecule embodiment of the invention that hybridizes under stringent conditions to the complement of the sequence of SEQ ID NO:2 or SEQ ID NO:3 corresponds to a naturally-occurring nucleic acid molecule.

EXAMPLES

Example 1

FIG. 1 shows the results of studies comparing adhesion of multipotent mouse mesenchymal stem cells, 10T1/2, to uncoated plastic and to plastic coated with various substrates. Adhesion is measured by the cell proliferation assay CELLTITER 96® AQ$_{ueous}$ Non-Radioactive Cell Proliferation Assay (MTS) sold by Promega, Inc. The CELLTITER 96® AQ$_{ueous}$ Non-Radioactive Cell Proliferation Assay is a calorimetric method for determining the number of viable cells in proliferation, cytotoxicity or chemosensitivity assays. The CELLTITER 96® AQ$_{ueous}$ Non-Radioactive Cell Proliferation Assay is composed of solutions of a tetrazolium compound (3-(4,5-dimethylthiazol-2-yl)-5-(3-carboxymethoxyphenyl)-2-(4-su-lfophenyl)-2H-tetrazolium, inner salt; MTS) and an electron coupling reagent (phenazine methosulfate) PMS. MTS is bioreduced by cells into a formazan that is soluble in tissue culture medium. The absorbance of the formazan at 490 nm can be measured directly from 96 well assay plates without additional processing. The conversion of MTS into the aqueous soluble formazan is accomplished by dehydrogenase enzymes found in metabolically active cells. The quantity of formazan product as measured by the amount of 490 nm absorbance is directly proportional to the number of living cells in culture.

No adhesion to uncoated plastic occurred during the 30 minute time period of this study. BSA (bovine serum albumin) and poly-L-lysine (PLL) were used as coating controls. Collagen I, a known adhesive protein substrate for these cells, served as positive control. Six synthetic peptides were conjugated to BSA and the conjugate coated onto plastic and tested for adhesion. A peptide fragment of osteopoentin ("OPN") that contained an RGD sequence failed to support adhesion. Synthetic peptides of 15-20 amino acids (without heparin sulfate attachment) from perlecan domains I, II, III, IV and V were tested and the results are shown in FIG. 1 under PLN1, PLN2, PLN3, PLN4, and PLN5 respectively. PLN4 represented a polypeptide of the amino acid sequence identified as SEQ ID NO:1. Five synthetic peptides of comparable length in amino acids failed to support adhesion (OPN, PLN1, 2, 3, 5). PLN4 provided an adhesion support comparable to collagen I.

Figure 2:
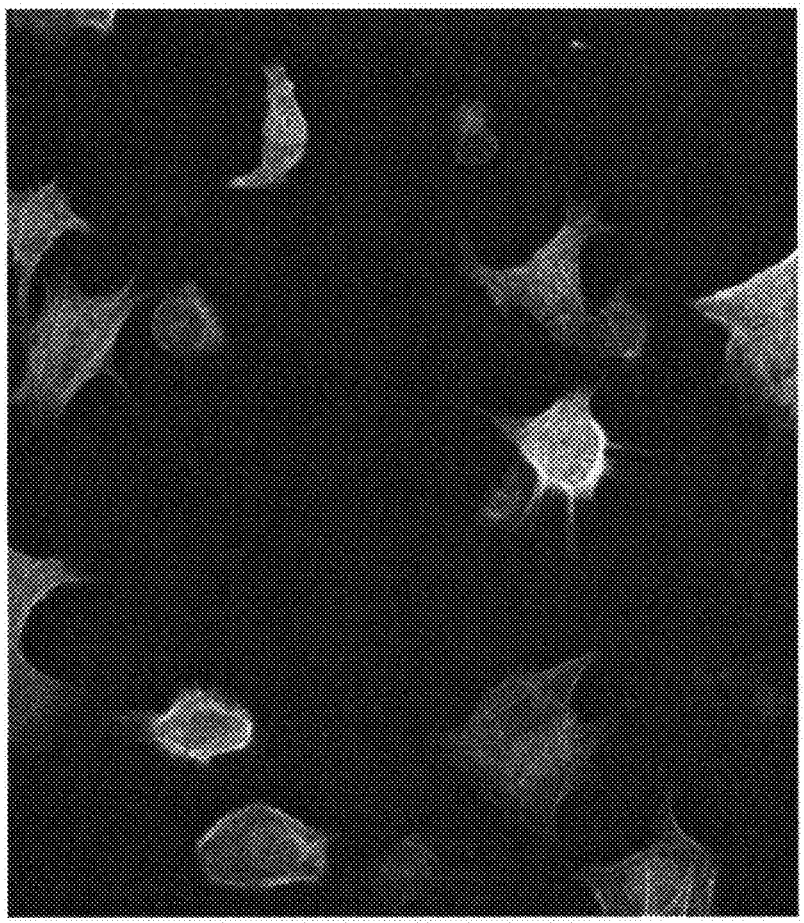
FIGS. 2 and 3 are photographs that show 10T1/2 cells plated on plastic coated with the polypeptide of SEQ ID NO: 1.
Figure 3:
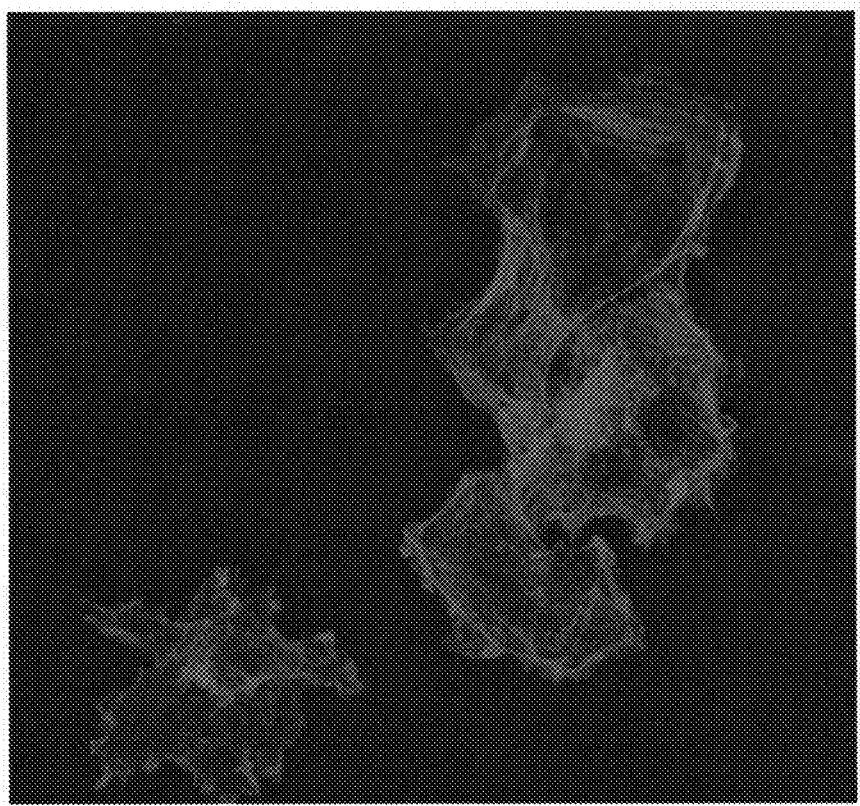
Figure 4:
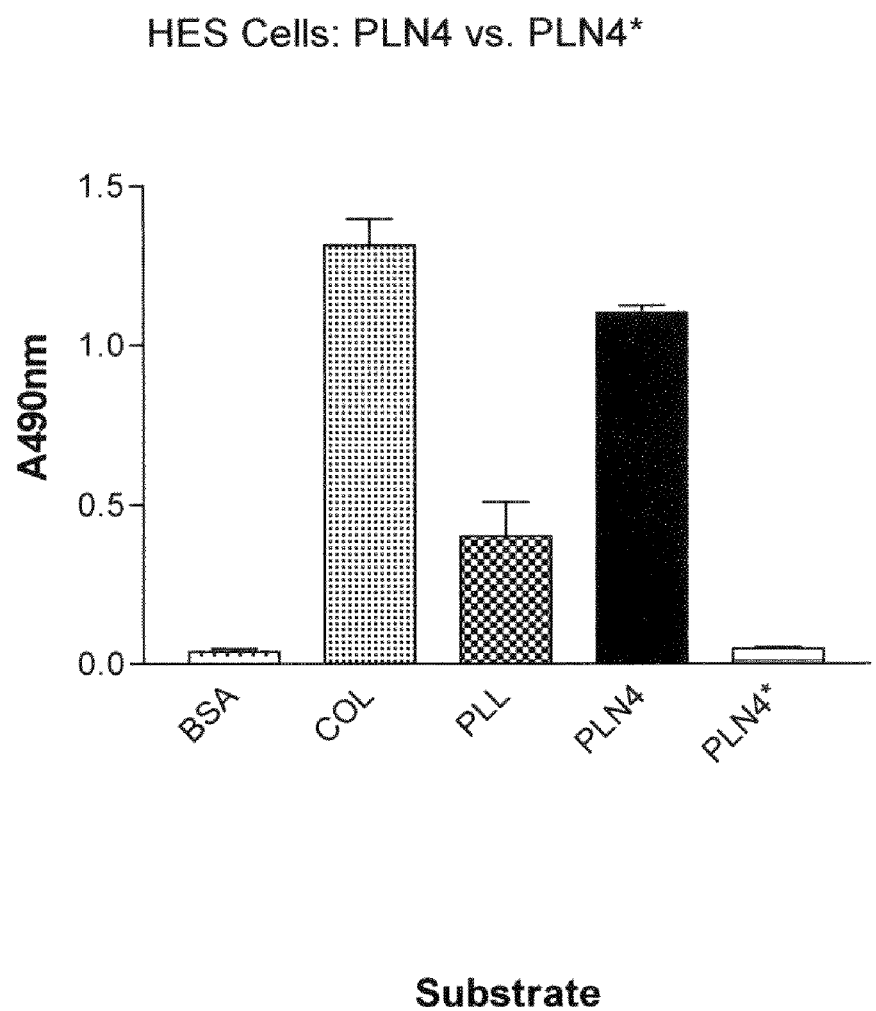
FIG. 4 is a bar graph depicting cell adhesion for the HES cell line on scaffolding coated with various substrates.
Figure 5:
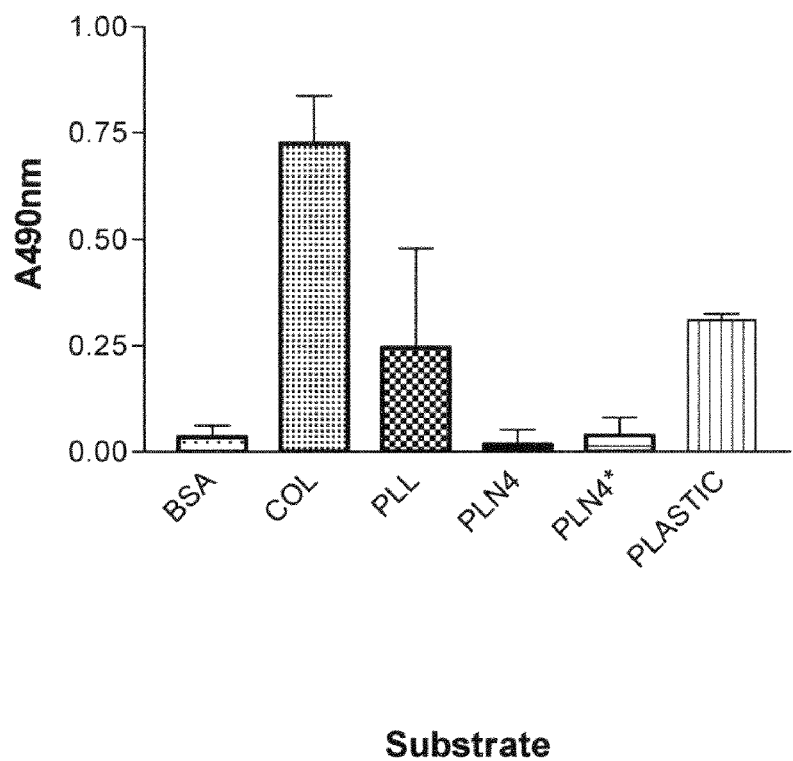
FIG. 5 is a bar graph depicting cell adhesion for the HS27a cell line on scaffolding coated with various substrates.
Figure 6:
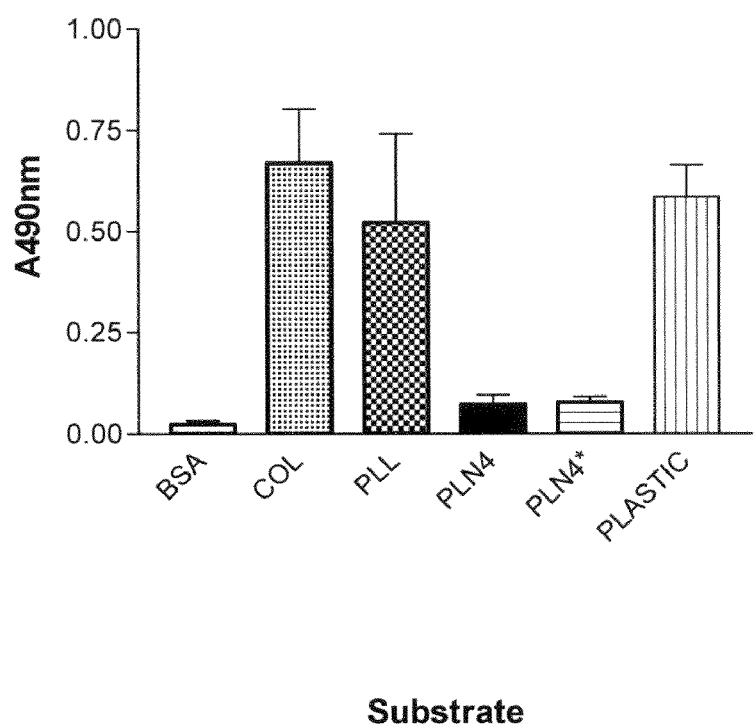
FIG. 6 is a bar graph depicting cell adhesion for the HS5 cell line on scaffolding coated with various substrates.
Figure 7:
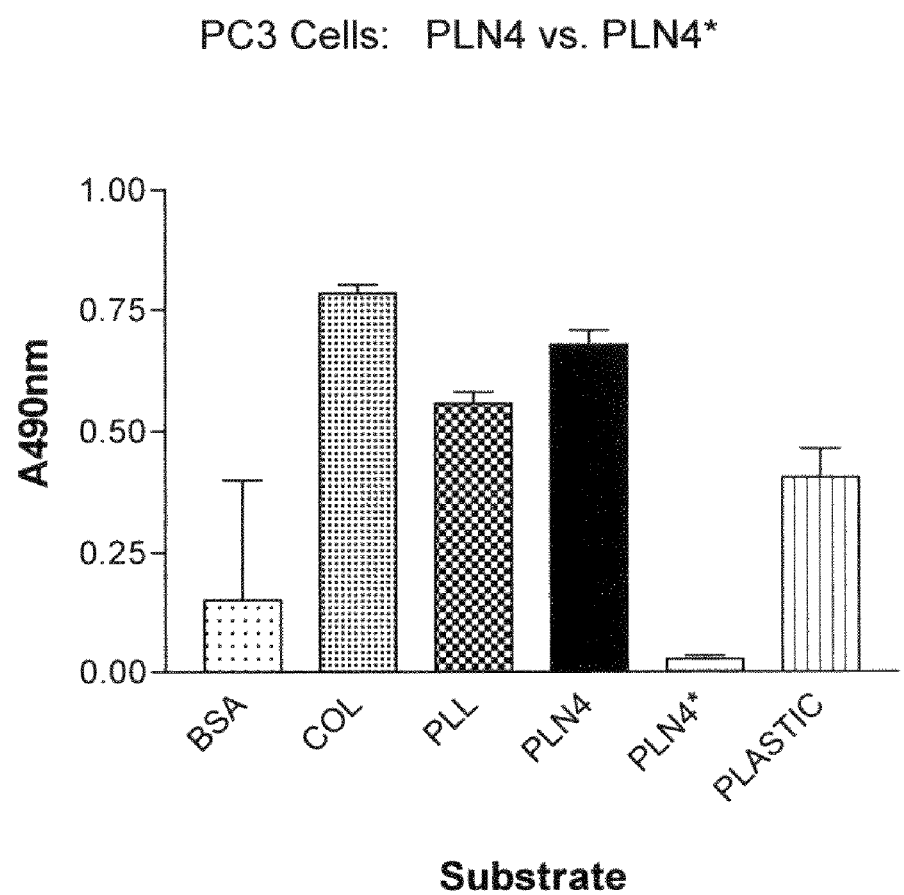
FIG. 7 is a bar graph depicting cell adhesion for the PC3 cell line on scaffolding coated with various substrates.
Figure 8:
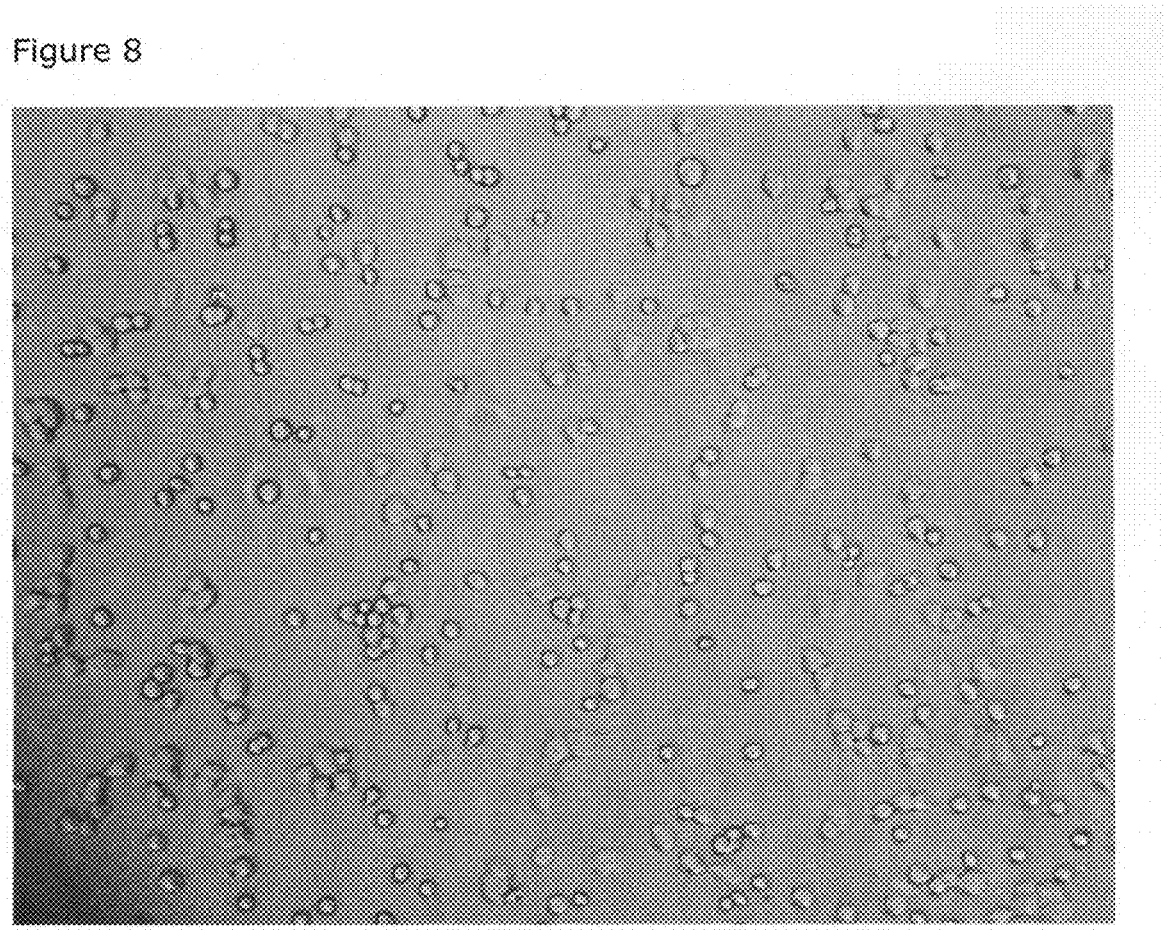
FIG. 8 is a photomicrograph showing HES cells attached and spreading on substrate coated with the polypeptide of SEQ ID NO:1.
Figure 9:
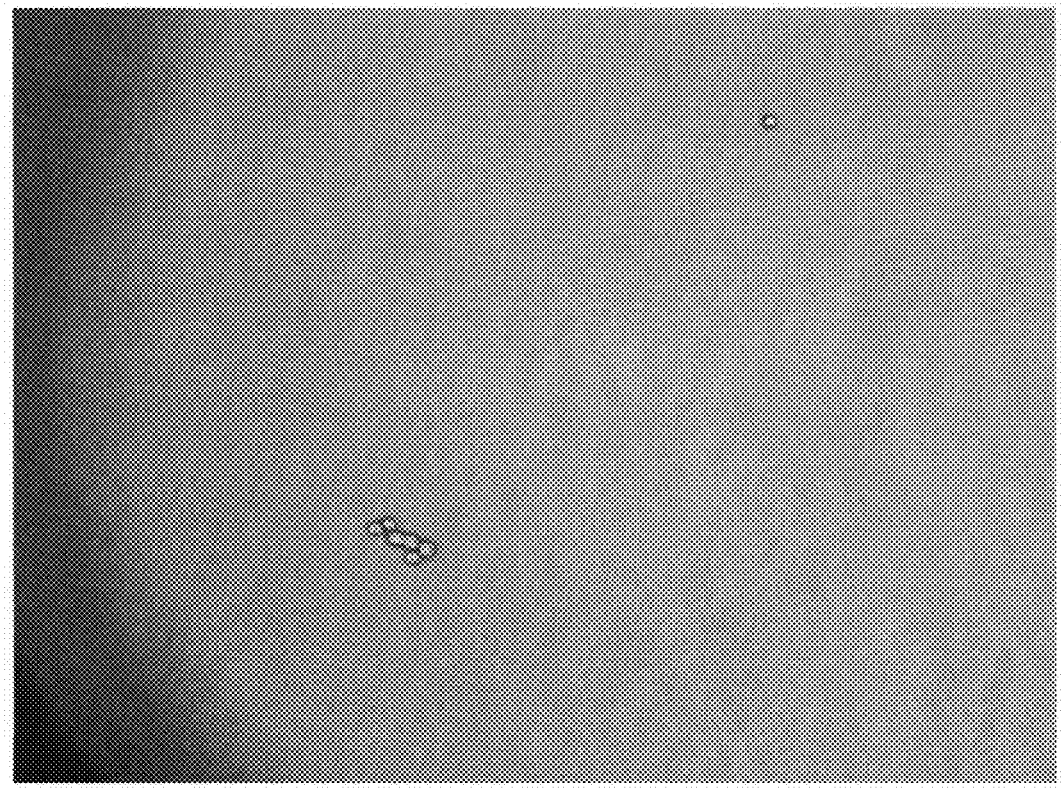
FIG. 9 is a photomicrograph showing HES cell attachment on a substrate coated with the polypeptide of SEQ ID NO:4.
Figure 10:
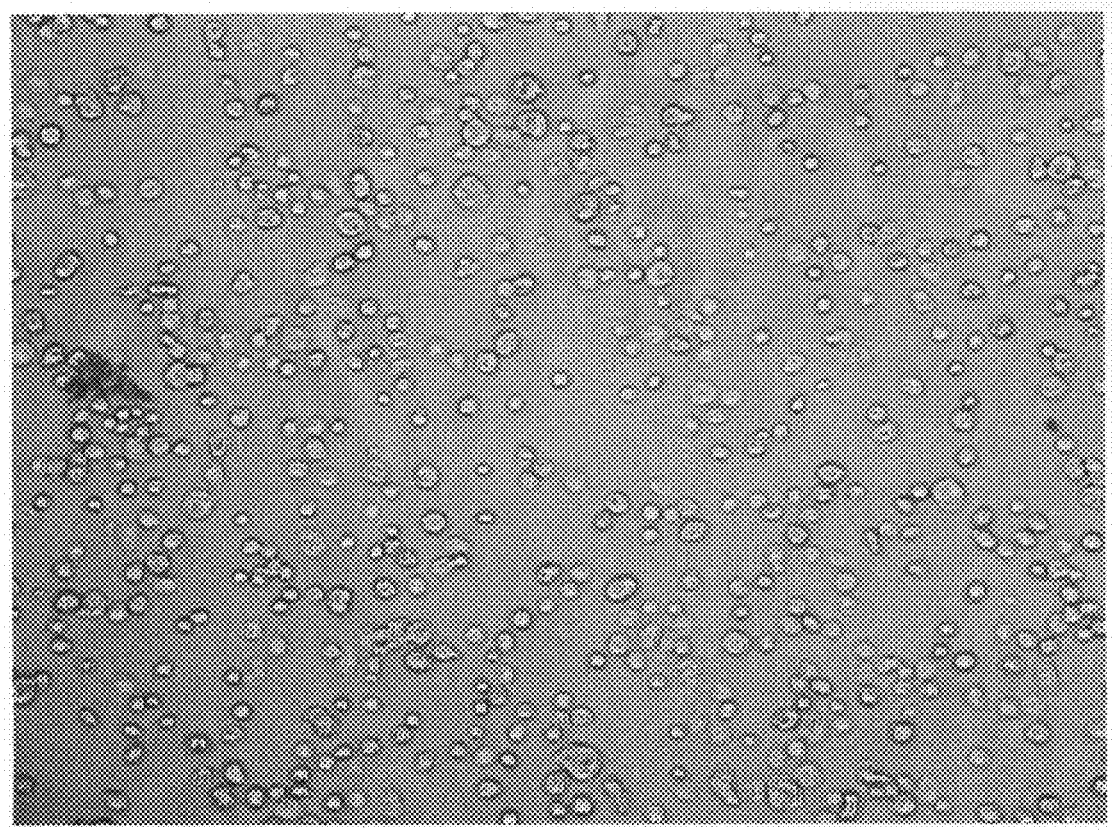
FIG. 10 is a photomicrograph showing PC3 cell attachment on a substrate coated with the polypeptide of SEQ ID NO:1.
Figure 11:
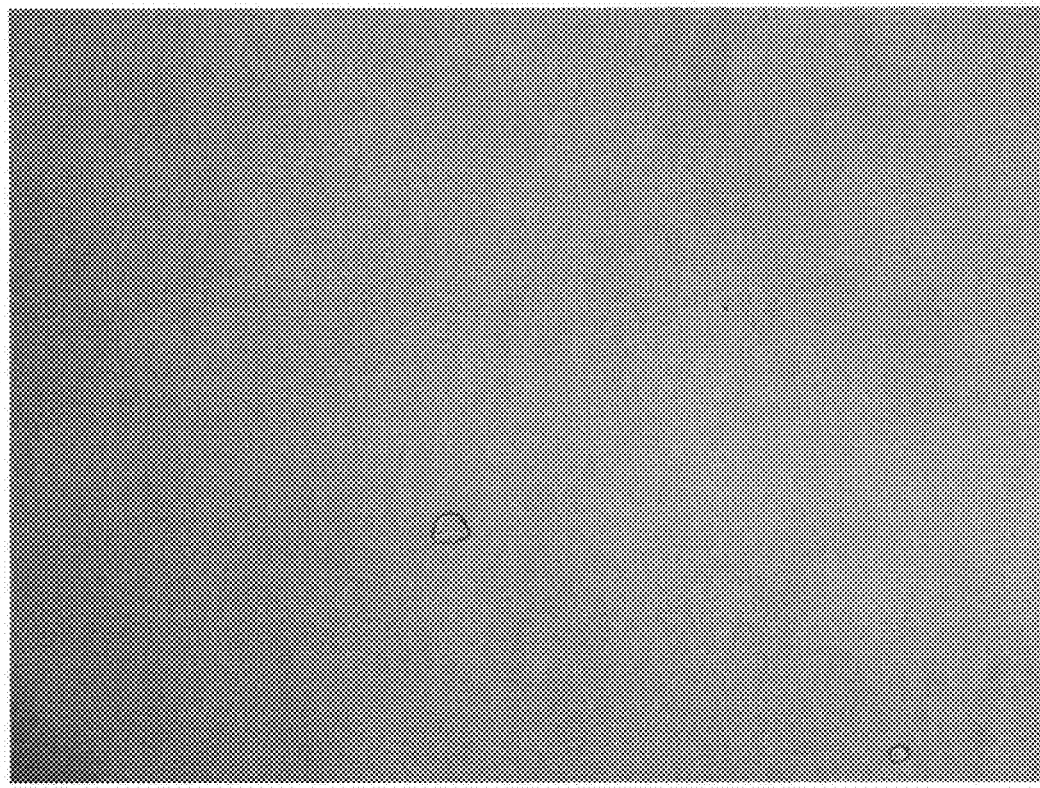
FIG. 11 is a photomicrograph showing PC3 cell attachment on a substrate coated with the polypeptide of SEQ ID NO:4.
Figure 12:
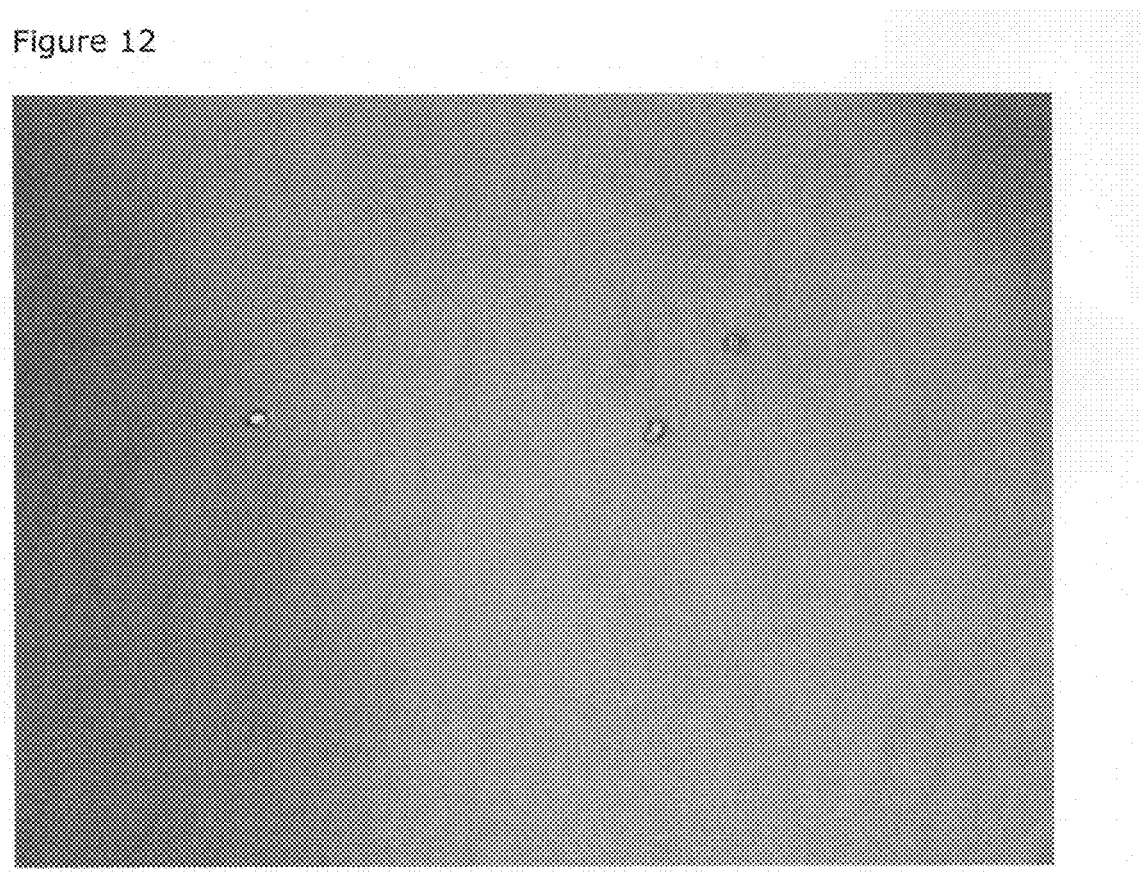
FIG. 12 is a photomicrograph showing HS27a cell attachment on a substrate coated with the polypeptide of SEQ ID NO:1.
Figure 13:
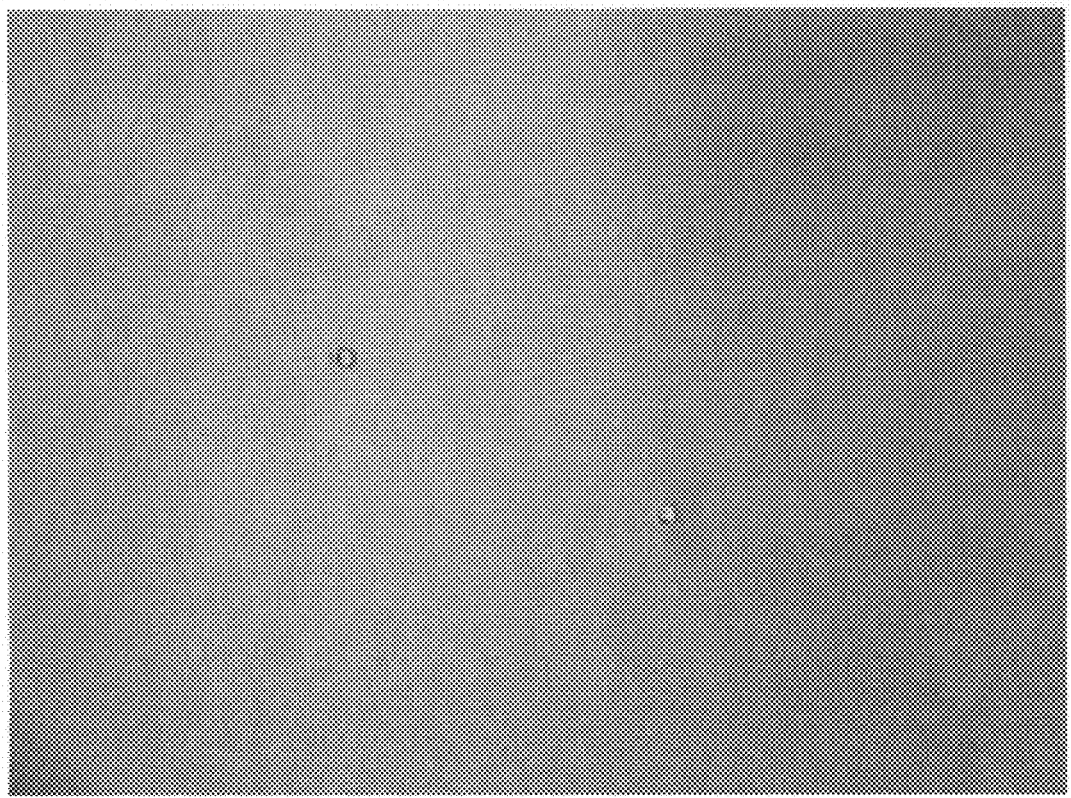
FIG. 13 is a photomicrograph showing HS27a cell attachment on a substrate coated with the polypeptide of SEQ ID NO:4.

FIGS. 2 and 3 are photomicrographs showing cellular adhesion of 10 T1/2 cells to plastic coated with BSA conjugated to the polypeptide of SEQ ID NO: 1. The photomicrographs show that adhesion is followed by focal adhesion formation. Cell binding activity to the surface coated with the polypeptide of SEQ ID NO:1 was consistent in repeat experiments and consistently strong.

Example 2

Cell Adhesion Assay

Concentrated stocks of rat-tail type I collagen were diluted to designated concentrations in 0.02 N acetic acid and coated overnight on MAXISORP® 96 well plates at room temperature (RT). Poly-L-lysine (PLL), heat-denatured bovine serum albumin (BSA), the peptide of SEQ ID NO:1 conjugated to BSA (indicated in FIGS. 4-7 as "PLN4") and a scrambled peptide from domain IV of perlecan having the amino acid sequence TGKSVGGSLIWPVRGQH (SEQ ID NO:4) conjugated to BSA (indicated in FIGS. 4-7 as "PLN4*") were diluted in 1×phosphate buffered saline (PBS) and also coated overnight on MAXISORP® 96 well plates at RT. The following day, the plates were washed three times with 1×PBS to remove any residue and blocked with 1% heat-denatured BSA for 1 hr at 37° C. Following blocking, plates were washed once with 1×PBS. Cells from various cell lines were harvested with 0.5 mM EDTA and collected by centrifugation. Pelleted cells were resuspended in serum-free RPMI 1640 and plated at a concentration of $2.5 \times 10^4$ cells per 100 µl. Cells were allowed to attach to the wells for 1 hr at 37° C. Next, the wells were washed once with 1% heat-denatured BSA to remove any unattached cells. Cell adhesion was quantified as in Example 1, using the CELLTITER 96® AQ$_{ueous}$ Non-Radioactive Cell Proliferation Assay (MTS). The cells were incubated with MTS for 3 hr at 37° C. Following incubation, an Elisa plate reader was used to measure optical density.

Amino acid sequence specificity of the adhesive properties of the polypeptide of SEQ ID NO:1 was confirmed by the observation that cell attachment and spreading did not occur using the scrambled peptide of SEQ ID NO:4 (indicated as PLN4* in FIGS. 4-7). In addition to sequence specificity, adhesion to the peptide of SEQ ID NO:1 was shown to be cell type-specific. FIGS. 4-13 show the results of adhesion tests following the above-described protocol using HES, HS27a, HS5, and PC3 cells. The two epithelia-derived cell lines, HES and PC3, showed the best adhesion and rapid focal adhesion formation of these four cell types. Well differentiated mesenchymal cells such as marrow stromal cells HS27a and HS5 did not bind to the peptide. The best adhesion of the cell types reported herein was shown with 10 T1/2 cells, reported in FIG. 1 and Example 1.

Although the inventions are illustrated and described herein with reference to specific embodiments, the inventions are not intended to be limited to the details shown. Rather, various modifications may be made in the details within the scope and range of equivalents of the claims and without departing from the inventions.

What is claimed:

1. An implantable device for adhering eukaryotic cells, the device comprising a scaffold coated with an isolated polypeptide, wherein said polypeptide is at least 90% identical to SEQ ID NO: 1 and exhibits adhesiveness to the eukaryotic cells, and wherein the scaffold comprises a synthetic polymer, a ceramic, a metal or combinations thereof.

2. The device of claim 1, wherein the polypeptide is attached to the scaffold by a linker.

3. The device of claim 2, wherein the linker is selected from the group consisting of bovine serum albumin, fibronectin, and collagen.

4. The device of claim 2, wherein the linker is selected from the group consisting of polyamides, polypeptides, polyesters, polycarbonates, polyurethanes, polyacetals, polysaccharides, and polyolefins.

5. The device of claim 2, wherein the linker is polylysine or polyalanine.

6. The device of claim 1, wherein the eukaryotic cells are selected from the group consisting of epithelial cells, epithelial stem cells, mesenchymal stem cells, and osteoblasts.

7. The device of claim 1, wherein the implanted device does not induce an inflammatory response.

8. The device of claim 1, wherein the polypeptide is phosphorylated.

9. A device providing a substrate for eukaryotic cell growth in vitro, the device comprising a scaffold coated with an isolated polypeptide, said polypeptide is at least 90% identical to SEQ ID NO: 1 and exhibits adhesiveness to the eukaryotic cells, wherein the polypeptide adheres the eukaryotic cells and provides support for eukaryotic cell replication and/or differentiation, and wherein the scaffold comprises a synthetic polymer, a ceramic, a metal or combinations thereof.

10. The device of claim 9, wherein the polypeptide is attached to the scaffold by a linker.

11. The device of claim 10, wherein the linker is selected from the group consisting of bovine serum albumin, fibronectin, and collagen.

12. The device of claim 10, wherein the linker is selected from the group consisting of polyamides, polypeptides, polyesters, polycarbonates, polyurethanes, polyacetals, polysaccharides, and polyolefins.

13. The device of claim 10, wherein the linker is polylysine or polyalanine.

14. The device of claim 9, wherein the eukaryotic cells are selected from the group consisting of epithelial cells, epithelial stem cells, mesenchymal stem cells, and osteoblasts.

15. The device of claim 9, wherein the polypeptide is phosphorylated.

* * * * *